US012458522B2

(12) United States Patent
Lovato et al.

(10) Patent No.: US 12,458,522 B2
(45) Date of Patent: Nov. 4, 2025

(54) NASAL DILATOR APPARATUS

(71) Applicants: Michelle Lovato, San Jose, CA (US); Rene S Lovato, San Jose, CA (US); Rene A Lovato, San Jose, CA (US)

(72) Inventors: Michelle Lovato, San Jose, CA (US); Rene S Lovato, San Jose, CA (US); Rene A Lovato, San Jose, CA (US)

( * ) Notice: Subject to any disclaimer, the term of this patent is extended or adjusted under 35 U.S.C. 154(b) by 349 days.

(21) Appl. No.: 15/050,428

(22) Filed: Feb. 22, 2016

(65) Prior Publication Data

US 2019/0167464 A1 Jun. 6, 2019

Related U.S. Application Data

(60) Provisional application No. 62/118,473, filed on Feb. 20, 2015.

(51) Int. Cl.

*A61F 5/08* (2006.01)
*A61F 5/56* (2006.01)
*A61M 29/00* (2006.01)

(52) U.S. Cl.

CPC .................. *A61F 5/08* (2013.01); *A61F 5/56* (2013.01); *A61M 29/00* (2013.01); *A61M 2210/0618* (2013.01)

(58) Field of Classification Search

CPC .... A61F 5/08; A61F 5/56; A61F 11/00; A61F 11/006; A61M 16/0666; A61M 16/0672; A61M 2210/0618; A61B 17/24

USPC .......................................................... 606/199

See application file for complete search history.

(56) References Cited

U.S. PATENT DOCUMENTS

2006/0260613 A1* 11/2006 Pinter ........................ A61F 5/08 128/206.11
2008/0178874 A1* 7/2008 Doshi ........................ A61F 5/08 128/200.24
2008/0190436 A1* 8/2008 Jaffe ................. A61M 16/0666 128/207.18
2011/0270297 A1* 11/2011 Judd .......................... A61F 5/08 606/199

* cited by examiner

*Primary Examiner* — Majid Jamialahmadi

(57) ABSTRACT

A removable nasal dilator device is configured and dimensioned for insertion into the nose to improve quality of breathing. The device may increase air flow through the nasal passage to lungs by helping maintain the nasal wall integrity, thus preventing the nasal passage from collapsing. It may also provide relief from snoring caused by mouth breathing when nasal passages are blocked. The nasal dilator apparatus is configured to fit over the bridge of the nose, curve over the edge of the nose, and fit comfortably inside the nasal passage. Loops, paddles or other terminal members on either end of the device maintain gentle outward pressure against the inside of the nasal wall to keep the nasal passage open.

12 Claims, 5 Drawing Sheets

FIG. 4

NASAL DILATOR APPARATUS

CROSS REFERENCE TO RELATED APPLICATIONS

This application claims the benefit of U.S. Provisional Application No. 62/118,473, filed Feb. 20, 2015, which is incorporated herein by reference in its entirety.

TECHNICAL FIELD

This invention relates to the field of health. More specifically, this invention relates to apparatus and methods for reducing snoring and improving quality of sleep.

BACKGROUND

Unless otherwise indicated herein, the approaches described in this section are not prior art to the claims in this application and are not admitted to be prior art by inclusion in this section. Each reference cited herein is incorporated by reference herein in its entirety.

There are many reasons for breathing problems: swollen turbinates, interior scaring, age, accident, or surgery all can cause the alar cartilage to lose some of it firmness and stability. Perhaps even the wearing of glasses can contribute to this condition. The narrowest part of the nose, called the ostium internum, located behind the nostril flare—the ala, is also the location of the nasal air passages to the lungs. When the lateral wall of the vestibule (immediately inside the entrance to the nostril) in the area of the ostium internum loses its firmness, the tissue becomes loose and draws inward with each inhalation of breath, thus effectively blocking off the air supply. The reverse is true with each exhalation, where the tissue is expanded outward.

In an effort to improve the air supply, a person may adjust his or her head and/or body position many times during the night and is often aware of a slight awakening which prevents the deep sleep required for REM (Rapid Eye Movement), the dream state—the deepest state of sleep. Without this REM state of sleep, sleep deprivation follows, leading to chronic fatigue and a sense of being tired even upon waking in the morning, also known as sleep apnea. Many sleepers simply give up and resort to mouth breathing, which leads to a whole new set of problems, the least of which is not increased snoring and dry mouth. Long periods of mouth breathing can lead to dental problems and increased interruption of sleep.

The medical profession has addressed the problem by operating upon those with enlarged turbinates, swollen tonsils and adenoids, which does not always correct the condition. Some devices have been employed for aiding in opening the nasal passage, such as nasal inhaler devices and coils, however their utility and efficacy remain in question and no practical nasal insertion devices are readily available.

Thus, there remains a need for devices and methods for improving the quality of sleep, for example by increasing the volume of air flow through the nasal passage, and reducing snoring caused by blocked or semi-blocked nasal passages.

SUMMARY

In some embodiments, a removable nasal device (some embodiments referred to herein as a Nasal Aid or Ultimate Nasal Dilator) can be inserted into the nose before sleep in order to increase the volume of air flow into the lungs, thus improving the quality of sleep and to reduce snoring caused by lack of air which often results in mouth breathing. In some embodiments, a nasal device may be constructed of medical grade stainless steel wire, or any material which has similar tensile strength and hygienic quality, flexibility and malleability, and may be formed into a plurality of arches including a bridge arch configured and dimensioned to fit over the bridge of the user's nose, with two arches curving over the nasal vestibule and two loops that rest on the ostium internum, the loops, slightly elliptical, run alongside the end of each of the two sides. The device is meant to benefit those who suffer from restricted air flow into the nasal passages due to shape or condition of the interior nostril areas and their cartilage support system, including enlarged turbinates. The device can also be worn during periods of inactivity.

In an example embodiment, a nasal device is adapted for insertion into the vestibule of a user's nose to maintain the integrity of the nasal wall for providing unobstructed air passages into the lungs in order to improve the quality of breathing and to reduce snoring. The device may include an arched shaped device constructed of a malleable or semi-malleable material having a desired tensile strength to maintain its shape and provide a biasing force within the nose to hold back tissues and keep the nasal passage open. In some embodiments a device may include three arches, left and right sides, with each side ending in a loop or terminal member which is adapted to rest sideways of the nasal passage near the alar sidewalls, the narrowest part of the nasal passage and the site of air blockage due to infirm tissue which draws inward with each inhalation of breath thus blocking the passage and causing an insufficient air supply, snoring, mouth breathing and poor quality of sleep. In some embodiments, such apparatus may also include features for retaining the arched shaped unit in position in a wearer's nose with a snug fit down the length of the nasal bridge, past the rhinion over the nasal sill and into the nasal vestibule coming to rest on the inside of the alar sidewall, with the loops or other terminal members serving as paddles to maintain and restrain tissue away from nasal air passages, and having the tensile strength in the material to maintain the given shape In some embodiments, terminal ends, e.g. configured as a paddle, blade or loop, may displace pressure from one point to all surfaces of said loops that come into contact with the nasal tissue, such construction being largely responsible for increasing a wearer's comfort and as an aid in maintaining placement of said device within a nose of a wearer.

In some embodiments, a nasal dilator device may be adjustable by the wearer for customizing for a particular nose by (a) widening or narrowing of the bridge arch spanning the nasal bridge the portion of the device that fits over the outside arch of the nose, (b) widening or closing the gap between said the arches that enter into the nasal vestibule, (c) widening or closing the gap between said nasal loops and the bridge frame, (d) slanting the loop arm inward or outward from the alar sidewall of the nose, and/or (e) increasing or decreasing depth of each loop by adjusting spaces between each said loop.

These as well as other aspects and advantages will become apparent to those of ordinary skill in the art by reading the following detailed description, with reference where appropriate to the accompanying drawings. Further, it should be understood that the embodiments described in this overview and elsewhere are intended to be examples only and do not necessarily limit the scope of the invention.

BRIEF DESCRIPTION OF THE DRAWINGS

For a better understanding of the nature and objects of the invention, reference should be made to the following detailed description taken in conjunction with the accompanying drawings, in which.

DETAILED DESCRIPTION

I. Overview

Described herein are apparatus and methods for improving airflow through a user's nose during breathing. In the following description, for purposes of explanation, numerous examples and specific details are set forth in order to provide a thorough understanding of the aspects of the systems and methods. It will be evident, however, to one skilled in the art that the present invention as defined by the claims may include some or all of the features in these examples alone or in combination with other features described below, and may further include modifications and equivalents of the features and concepts described herein.

In some embodiments, an Ultimate Nasal Dilator apparatus is a removable device designed to be inserted into the nose to improve quality of breathing. This device may be used to increase air flow through the nasal passage to lungs by helping maintain the nasal wall integrity, thus preventing the nasal passage from collapsing. For example, when inserted into the nose, distal arms and terminal members may provide and outward biasing force against the interior of the nasal wall to help keep the nasal passage open to air flow. In some embodiments, nasal dilator apparatus described herein may provide relief from snoring caused by mouth breathing, e.g., resulting when the nasal passages are blocked.

In some embodiments, the shape of the Ultimate Nasal Dilator is designed to worn comfortably over the bridge of the nose, curve over the edge of the nose, and fit comfortably inside the nasal passage. The loops, or other terminal members, on either end of the device then press gently against the inside of the nasal wall to keep nasal passages open.

In some embodiments, the device is adjustable by narrowing or widening different portions or structural members of the apparatus, such as narrowing or widening the arch the fits over the bridge of the nose, narrowing or widening the gap between the curves that go over the edge of the nostril, opening or closing the gap between the end loops and the nasal bridge frame, or moving in or out the slant of the loops to accommodate the size of the nasal passage.

II. Example Embodiments

Figure 1:
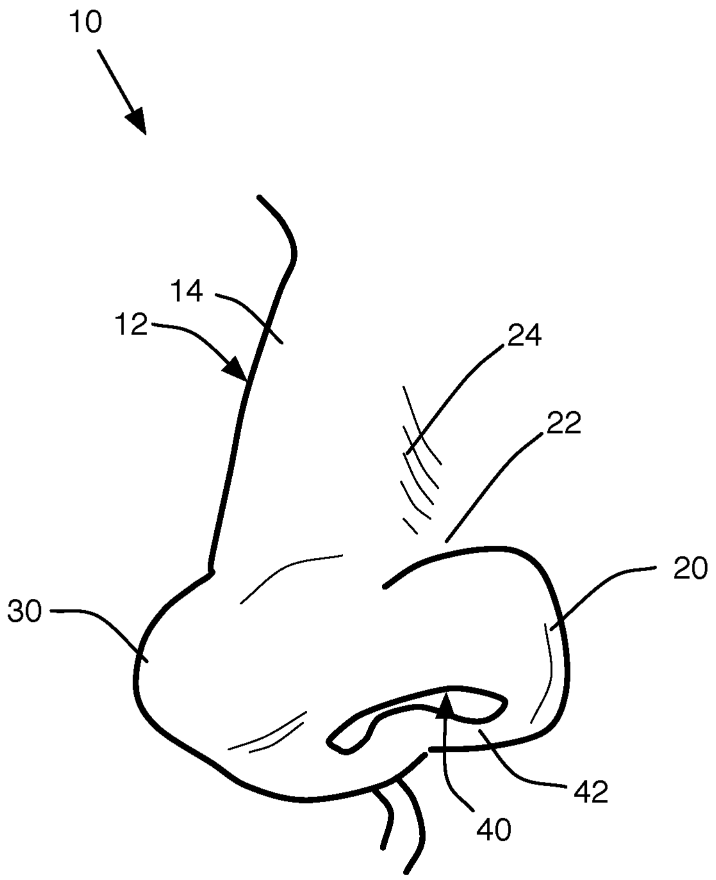
FIG. 1 is a side view schematic illustration of a nose, showing anatomical features that may be helpful in describing use of various embodiments of nasal dilator apparatus herein.

In the following detailed description, various embodiments are shown and described with reference to various anatomical features of a human nose. To aid in this discussion, FIG. 1 is provided as a side view illustration of a human nose 10 with certain anatomical features shown, including the nasal bridge 12, apex 30, ala (or nostril flare) 20, and naris (also referred to as the nostril) 40. On the nasal bridge 12, the area where bone meets cartilage (also described as the osseocartilaginous junction or the anterior tip of the median suture joining the nasal bones) is referred to herein as the rhinion 14. Near the base of the nose sidewall 24 where it meets the ala 20, is the alar crease 22. The edge of the naris opening is sometimes referred to herein as the nasal sill 42.

Each naris 40 or nostril provides an opening to the nasal cavity. The term "nasal passage" is also used herein to refer to the passageway or channel within the nasal cavity for air to flow through the nose. The area just inside each ala 20, through the naris 40, is sometimes referred to herein as the vestibule. Also, the area of the nasal passage just under the alar crease 22 and lower sidewall 24 is also sometimes referred to herein as "ostium internum", which is sometimes described as the narrowest portion of the nasal passage and which in some people may loses its firmness or elasticity such that the nasal passage may draw inward with each inhalation of breath and restrict or block flow of air through the nasal passage to a user's lungs. Apparatus and methods described herein may be used to provide additional support to prevent airflow obstruction and maintain patency of the nasal passage.

Figure 2:
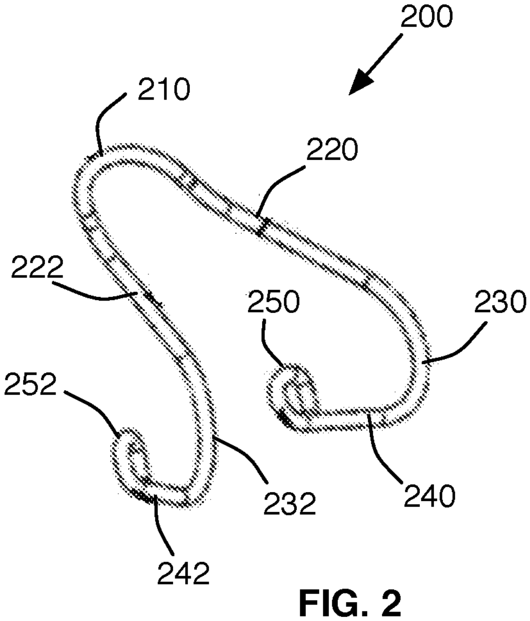
FIG. 2 is a perspective view illustration of a nasal dilator apparatus in accordance with an example embodiment.

Turning now to FIG. 2, a nasal dilator apparatus 200 according to one embodiment may be an elongated wire or other structure, e.g., constructed of stainless steel (e.g., medical grade stainless), other metals or metal alloys, plastic, Teflon, neoprene, nylon, polystyrene, PVC, or any combination there of. Apparatus 200 may include a nose bridge arch 210 configured to fit over the bridge of the nose and a pair of terminal members 250, 252, e.g., loops, paddles, blades, or other terminal members configured and dimensioned to fit through each nostril and rest within the nasal passage of a user to press against an outer wall of the passage (e.g., in the area of the ostium internum). Each terminal member 250, 252 is connected to the nasal bridge by a nostril arm 240, 242, a nostril arch 230, 232, and a pair of bridge arms 220, 222 configured to fit on each side of the nose.

Figure 3:
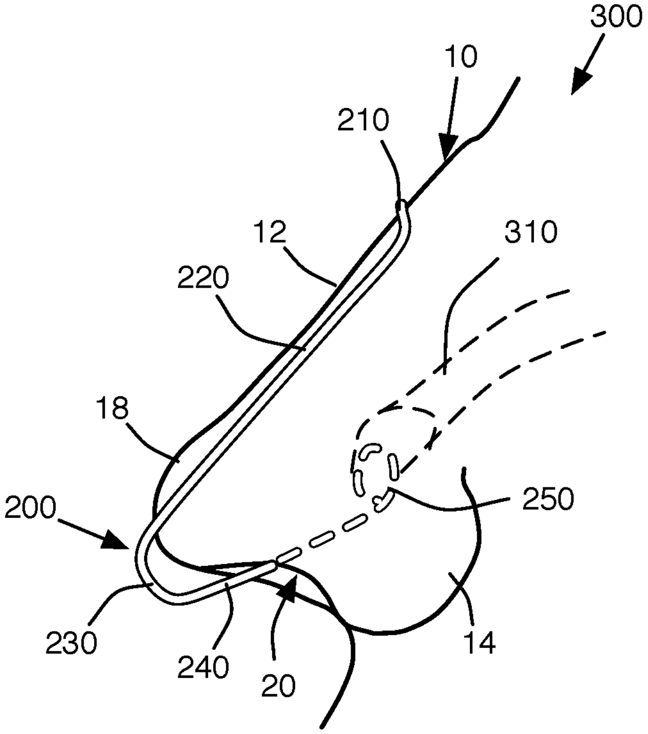
FIG. 3 is a side view of a nasal dilator apparatus of FIG. 2 in use in a nose of a user in accordance with an example embodiment.

Referring to FIG. 3, a method 300 of using a nasal dilator device 200 is shown in a profile view of a nose 10. Device 200 includes bridge arch 210 over bridge 12 of nose, with the left bridge arm 220 along the side of nose and next to the apex 30. The nostril arch 230 is bent such that nostril arm 240 is directed through nostril 40. Terminal member 250, here shown as a loop, is inserted into the nasal cavity to press against the inner alar wall in the region of the ostium internum 312. To insert the device 200, bridge arms 220, 222 may be pinched slightly to provide inward displacement of arms 240, 242 and terminal members 250, 252 during insertion. When inserted and released, the bridge arms move back into position and provide a biasing force for terminal members 250, 252 against the interior tissues of the nose to maintain patency and airflow through nasal passage 310.

Figure 4:
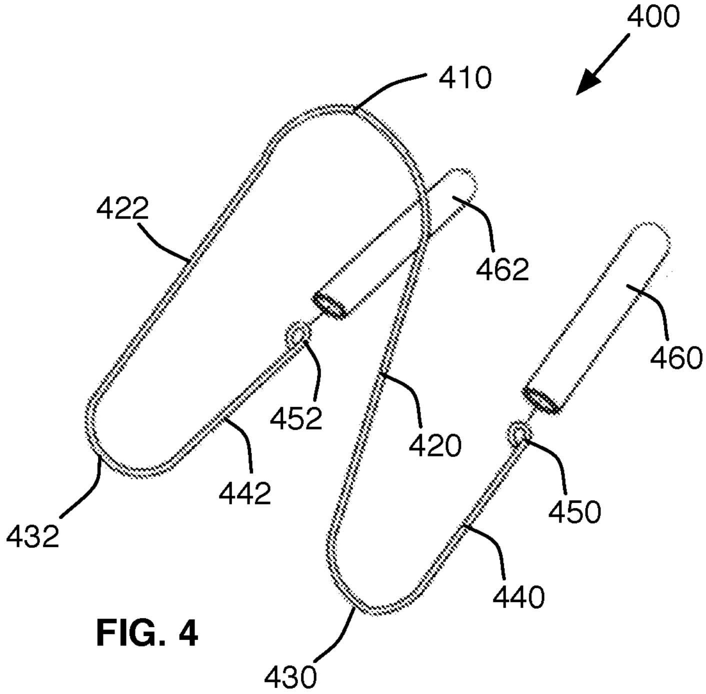
FIG. 4 is a front perspective view of a nasal dilator apparatus in accordance with another example embodiment.

FIG. 4 shows another embodiment of a nasal dilator device 400 according to an example embodiment. Like device 200, device 400 may include a wire-shaped body having a bridge arch 410 connecting a pair of bridge arms 420, 422, nostril arches 430, 432, and nostril arms 440, 442. Each arm 440, 442 may terminate in a terminal member 250, 252, e.g., to provide a desired surface area and/or comfort when arms 440, 442 spread and press against the inner surface of the outer region of each ala. Additionally, one or more comfort tips 460, 462, may be placed over each nostril arm 440, 442 and/or terminal member 250, 252 to provide further comfort when the nostril arms 440, 442 rest in the nasal passages. In some embodiments, tips 460, 462 may be silicone, neoprene, plastic, other elastomeric material, or some other desired material to provide optimal comfort and cleanliness.

Figure 5:
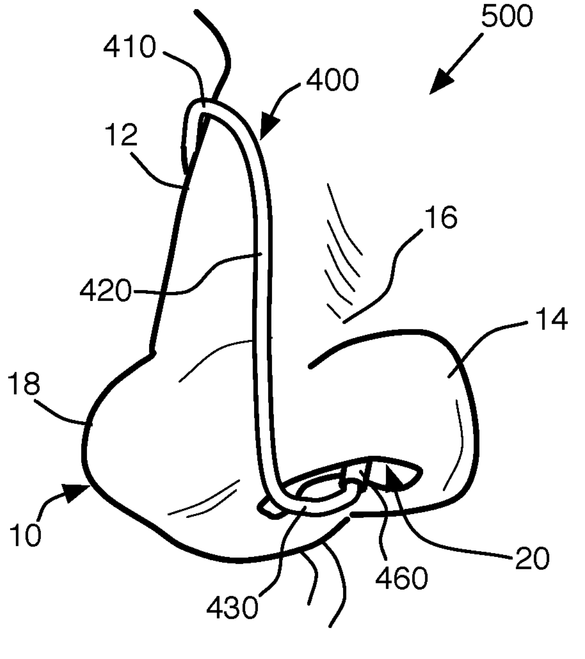
FIG. 5 is a side perspective view of an example nasal dilator apparatus of FIG. 4 in use in a nose of a user in accordance with an example embodiment.

Referring to FIG. 5, a method 500 of using a nasal dilator device 400 is shown in a perspective view of a nose 10. Device 400 may include bridge arch 410 configured to fit snugly over bridge 12 of the nose, with the left bridge arm 420 along the side of nose and each side of the apex 30. The nostril arch 430 is bent around the nasal sill such that nostril arm (not shown) is directed through the naris 40 and rests within the nasal passage. Comfort tip 460 is shown extending from the nasal cavity and pressing against the inner surface of the ala 41 wall.

Figure 6:
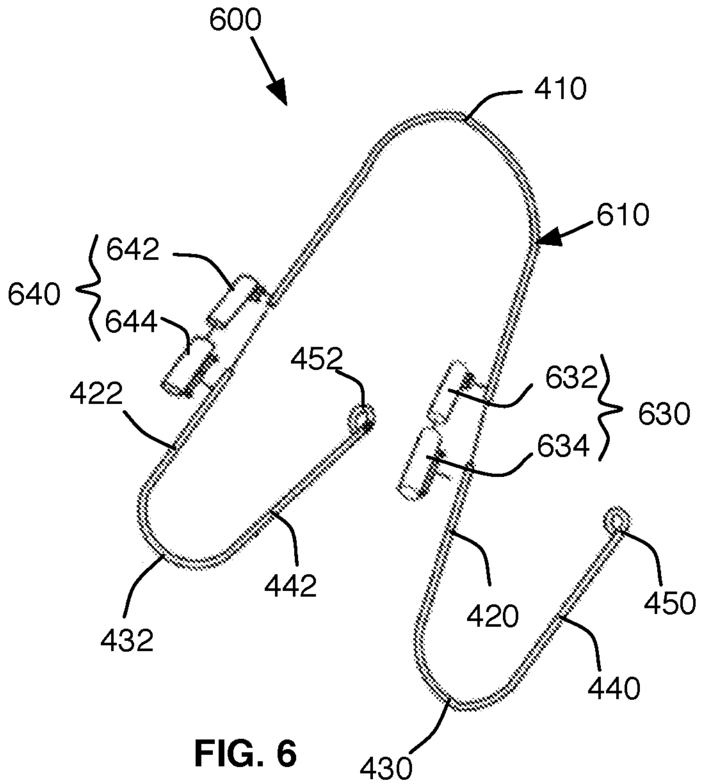
FIG. 6 is a perspective view of another example nasal dilator apparatus that is adjustable in a vertical direction, in accordance with an example embodiment.
Figure 7:
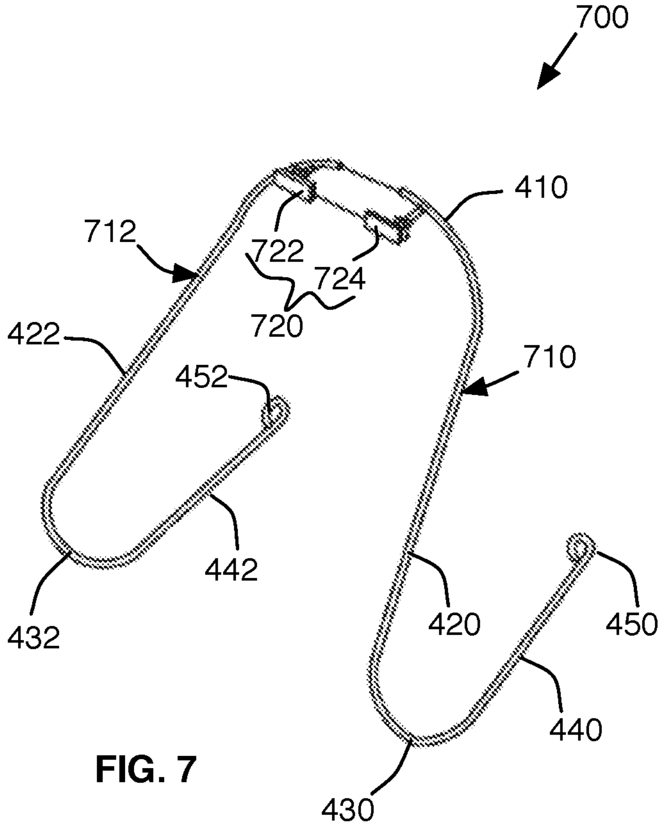
FIG. 7 is a perspective view example of another example nasal dilator apparatus that is adjustable in a horizontal direction, in accordance with an example embodiment.

Turning now to FIGS. 6 and 7, example embodiments of adjustable nasal dilator devices 600, 700 are shown. In some embodiments, a device 600 or 700 may have all of the features of device 400, but also may include one or more adjustment assemblies, e.g., vertical adjustment assemblies 630, 640 (FIG. 6) and/or horizontal adjustment assembly 720 (FIG. 7).

For example, referring to FIG. 6, device 600 may be comprised of multiple main pieces that may be coupled and/or adjusted as desired, for example a bridge segment 610 and two nostril segments 620, 622. In this example, the bridge segment 600 may include a bridge arch 410 as described above and one or more and one or more bridge arm segments 420, 422. Left nostril segment 620 may include a bridge arm segment 420' (which may be adapted to adjustably couple to segment 420), nostril arch 430, arm 440 and terminal member 450. Similarly, right nostril segment 622 may include a bridge arm segment 422'(which may be adapted to adjustably couple to segment 422), nostril arch 432, arm 442 and terminal member 452. Each vertical adjustment assembly 630, 640 may include features to adjustable couple the bridge segment 610 with each nostril segment 620, 622, such that the lengths of arms 420+420' and 422+422' may be varied as desired for different size noses and/or fit preferences. In some embodiments, each adjustment assembly 630, 640 may include one or more vertical extending devices 632, 634 and 642, 644, respectively configured to slideably or otherwise adjustably secure to each other at a desired length. In some embodiments, one or more connectors 633, 635 and 643, 645, respectively, may be used to connect each extending device or coupler to the respective arm segment 420, 420', 422, 422'. In some embodiments, corresponding extending devices 632, 634 may be similar in shape (e.g., cylindrical or other elongated shape) but with different diameters such that one device, (e.g., 632) fits within the other, (e.g., 634), for example such as a screw and elongated nut with corresponding threads. In other embodiments, other extending device shapes and/or coupling or extension mechanisms may be employed (e.g., using tabs, stops, ribs, or other features).

Referring to FIG. 7, a perspective view example of a nasal dilator apparatus 700 that is adjustable in a horizontal direction is shown. In this example, a horizontal extending assembly 720 is attached to the nose bridge arch region 410. In such embodiments, two segments, e.g., a left segment 710 and a right segment 712, may be adjustably coupled by the assembly 720. As described above with respect to device 600 of FIG. 6, assembly 720 may include one or more horizontal extending devices 722, 724 that may be configured to engage each other. For example, each device 722, 724 may be elongated, cylindrical or oblong in shape, and may be dimensioned to fit together (e.g., using threads, tabs, stops, notches, or other desired features) and adjusted as desired for snugness and fit across the bridge of the user's nose.

Figure 8:
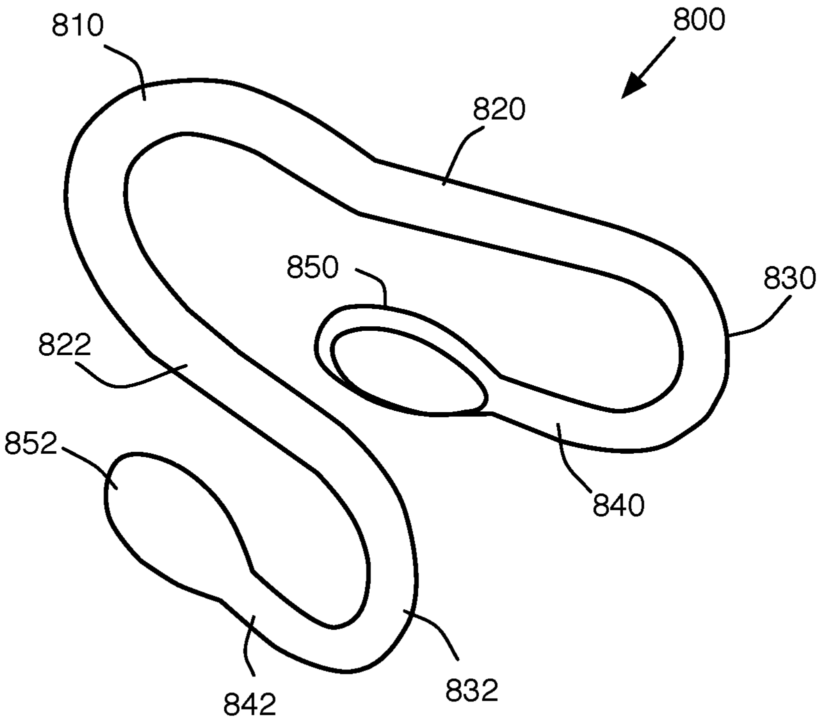
FIG. 8 is a perspective view illustration of another example embodiment of a nasal dilator apparatus having closed loop terminal members.

Turning now to FIG. 8, another embodiment of a nasal dilator apparatus 800 is shown. In this embodiment, device 800 may be configured and dimensioned as a unibody structure constructed or comprised of any desired material or combination of materials, e.g. plastic, resin, PVC, Teflon, polystyrene, silicone, neoprene, nylon, or other desired material. In some embodiments, device 800 may be molded or formed as a uniform material. In other embodiments, device 800 may be comprised of any combination of materials and/or pieces, e.g., stainless steel or other core material coated with a resin, silicone, neoprene, plastic, Teflon, or other desired material. Similar to other embodiments described herein, device 800 may include a bridge arch 810 configured to fit over the bridge of a user's nose, arms 820, 822, nostril arches 830, 832, arms 840, 842, and terminal members 850, 852. In some embodiments, device 800 may be configured and dimensioned to have a desired rigidity to provide outward biasing force of terminal members 850, 852 and arms 840, 842 against the interior surfaces of nose to facilitate opening of nasal passages when inserted into the nose of a user. Biasing members 850, 852, may be constructed and dimensioned to have a smooth outer surface for optimal comfort when in contact with the tissue membranes within the nose, e.g., using rounded edges, and may be configured in the shape of a paddle, blade, or other desired shape (e.g., with curved or concave dimensions to provide optimal comfort and minimal bulk to facilitate flow of air through the nasal passages. In some embodiments, portions of device body 800 that contact a user's skin, e.g., an inner surface of bridge arch 810 or bridge arms 820, 822 may be flattened or otherwise dimensioned to optimize comfort and minimize pressure points against the user's skin.

The foregoing description illustrates various embodiments of nasal dilator apparatus, along with examples of how aspects may be implemented. The above examples and embodiments should not be deemed to be the only embodiments, and are presented to illustrate the flexibility and advantages of the present invention. Based on the above disclosure and the following claims, other arrangements, embodiments, implementations and equivalents will be evident to those skilled in the art and may be employed without departing from the spirit or scope of the subject matter presented herein. It will be readily understood that the aspects of the present disclosure, as generally described herein and illustrated in the figures, can be arranged, substituted, combined, separated, and designed in a wide variety of different configurations, all of which are explicitly contemplated herein.

What is claimed is:

1. A nasal dilator apparatus, comprising:

a wire-shaped body including:

a bridge arch connecting a pair of bridge arms, a pair of nostril arms, each nostril arm of the pair of nostril arms are connected to one of the pair of bridge arms by a nostril arch, and a terminal loop at an end of each nostril arm of the pair of nostril arms; and at least two cylindrical comfort tips, each comfort tip of the at least two cylindrical comfort tips is configured and dimensioned to be placed over one of the terminal loops and its corresponding nostril arm of the pair of nostril arms.

2. The nasal dilator apparatus of claim 1, wherein the bridge arch and the bridge arms are constructed of a rigid or semi-rigid material and dimensioned to provide an outward biasing force of each of the terminal loops against nasal passages of a user when the apparatus is inserted in the user's nose.

3. The nasal dilator apparatus of claim 2, wherein the bridge arch, the bridge arms, the nostril arches, the nostril arms, and the terminal loops comprise a unibody structure.

4. The nasal dilator apparatus of claim 3, wherein the unibody structure comprises stainless steel polytetrafluoroethylene, nylon, neoprene, polystyrene, silicone, PVC, or a combination thereof.

5. The nasal dilator apparatus of claim 1, further comprising one or more adjustment assemblies secured to the body to selectively adjust a length of one or more of the bridge arch, the bridge arms, the nostril arches, or the nostril arms.

6. The nasal dilator apparatus of claim 5, wherein each of the one or more adjustment assemblies comprises a pair of horizontal extending devices configured to slidably couple with one another, and wherein each horizontal extending device of the pair of horizontal extending devices is secured to a different segment of the bridge arch.

7. The nasal dilator apparatus of claim 5 wherein each of the one or more adjustment assemblies comprises a pair of vertical extending devices on each bridge arm of the pair of bridge arms, wherein each vertical extending device of the pair of vertical extending devices is configured to slidably couple with the other corresponding vertical extending device in the respective pair of vertical extending devices, and wherein each vertical extending device of the pair of vertical extending devices is secured to a different segment of one of the bridge arms.

8. The nasal dilator apparatus of claim 1, wherein the apparatus is configured to be adjustable by a wearer by:

(a) widening or narrowing of the bridge arch, (b) widening or closing a gap between the nostril arches, (c) widening or closing a gap between each of the terminal loops and a corresponding bridge arm of the pair of bridge arms, (d) slanting the terminal loops inward or outward from an alar sidewall of a nose, (e) varying a dimension of the terminal loops, or (f) a combination of adjustments selected from (a), (b), (c), (d), and (e).

9. The nasal dilator apparatus of claim 1, wherein the body comprises a stainless steel wire that is bent to form the bridge arch, the bridge arms, the nostril arms, and the terminal loops.

10. A nasal dilator apparatus, comprising:

an elongated body having a central bridge arch adapted fit over a bridge of a nose, left and right bridge arms extending from opposite ends of the central bridge arch, left and right nostril arms extending respectively from the left and right bridge arms and adapted to be inserted into a nostril of the nose, and left and right terminal loops at a distal end of each of the left and right nostril arms, respectively; and at least two cylindrical comfort tips, each comfort tip of the at least two cylindrical comfort tips is adapted to slide over one of the left and right terminal loops and its corresponding nostril arm of the left and right nostril arms.

11. The nasal dilator apparatus of claim 10, wherein the elongated body comprises a stainless steel wire forming the bridge arch, the bridge arms, the nostril arms, and the terminal loops.

12. The nasal dilator apparatus of claim 11, wherein each of the at least two cylindrical comfort tips comprises a silicone sleeve having an open end configured and dimensioned to be placed over one of the nostril arms.

* * * * *